(12) United States Patent
Fei et al.

(10) Patent No.: US 7,698,945 B2
(45) Date of Patent: Apr. 20, 2010

(54) SYSTEM AND METHOD FOR DETECTING INTERNAL FLAWS IN A PARTICULATE FILTER

(75) Inventors: Dong Fei, Peoria, IL (US); Jade Katinas, Chillicothe, IL (US); Leonard G. Wheat, Manito, IL (US); Linxiao Yu, Peoria, IL (US); Douglas A. Rebinsky, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 139 days.

(21) Appl. No.: 11/983,282

(22) Filed: Nov. 8, 2007

(65) Prior Publication Data

US 2009/0120189 A1 May 14, 2009

(51) Int. Cl.
*G01N 29/00* (2006.01)
(52) U.S. Cl. .............................. 73/596; 73/600; 73/602; 73/644
(58) Field of Classification Search .................. 73/644, 73/618, 622, 625, 627, 629, 635, 639, 641, 73/866.5
See application file for complete search history.

(56) References Cited

U.S. PATENT DOCUMENTS 3,712,119 A * 1/1973 Cross et al. .................... 73/614
4,319,840 A 3/1982 Kondo et al.
4,961,346 A * 10/1990 Salvado et al. ................ 73/644
5,102,434 A * 4/1992 Hijikata et al. ................ 95/273
5,419,181 A 5/1995 Egan et al.
6,032,534 A * 3/2000 Sherwin ....................... 73/628
6,840,083 B2 1/2005 Hijikata
6,880,403 B1 * 4/2005 Shimada et al. ............... 73/652
6,964,694 B2 11/2005 Rauchfuss et al.
7,234,355 B2 6/2007 Dewangan et al.
2004/0007077 A1 1/2004 Hijikata
2007/0144260 A1 6/2007 Fei et al.
2007/0266789 A1 11/2007 Hampton

FOREIGN PATENT DOCUMENTS

DE 2930508 2/1981
DE 10160944 7/2003
JP 2004151078 5/2004

* cited by examiner

*Primary Examiner*—J M Saint Surin
(74) *Attorney, Agent, or Firm*—Liell & McNeil

(57) ABSTRACT

A method of detecting an internal flaw in a particulate filter includes a step of coupling ultrasonic transducer with the particulate filter. The method also includes a step of moving at least one of the ultrasonic transducer and the particulate filter relative to the other. Consistent coupling of the ultrasonic transducer with the particulate filter is maintained during the moving step. Ultrasonic energy is transmitted from the ultrasonic transducer through a majority of a volume of the particulate filter. The method also includes a step of determining if the particulate filter includes an internal flaw using the ultrasonic energy.

16 Claims, 3 Drawing Sheets

SYSTEM AND METHOD FOR DETECTING INTERNAL FLAWS IN A PARTICULATE FILTER

TECHNICAL FIELD

The present disclosure relates generally to detecting internal flaws in a particulate filter using ultrasonic energy continuously transmitted through the particulate filter while one of the particulate filter and an ultrasonic transducer is moved relative to the other, and more particularly to maintaining consistent coupling of the ultrasonic transducer with the particulate filter during the movement.

BACKGROUND

Recent governmental regulations have prompted development and application of exhaust aftertreatment systems to reduce particulate matter emissions from both on-highway and off-highway vehicles. Exhaust aftertreatment systems for diesel engines, for example, typically include a diesel particulate filter. Particulate filters, such as a diesel particulate filter, typically include a cylindrical shape with a honeycomb structure cross section. Generally, these honeycomb structures are formed by bringing a powder of ceramic, metal or the like together with a binder, and extruding the mixture with a honeycomb shape. This structure is then fired to fix the honeycomb shape.

Filtration occurs by passing exhaust gas through walls of the honeycomb structure while trapping particles. In some instances, these filters may then be coated with a suitable catalyst to facilitate exhaust aftertreatment of other constituents, such as by the inclusion of a diesel oxidation catalyst for oxidizing hydrocarbons and carbon monoxide to carbon dioxide gas and other more desirable compounds. It is well known that, during the production process, occasional internal defects, such as cracks and internal voids, can sometimes occur in the honeycomb structures of the particulate filters. When a crack occurs in cell walls of the particulate filter, the crack can significantly affect the durability of the particulate filter and can result in a substantial deterioration in the ability of the filter to trap particles, at least in the area of the crack, according to expectations and specifications. Visual inspections have proven an inadequate strategy for detecting internal flaws in particulate filters.

It is known to employ an ultrasound testing strategy to detect internal flaws in particulate filters. For example, in the testing strategy described in U.S. Publication No. 2007/0144260, a test apparatus may include one or more ultrasound transducers for performing either a pulse echo test or a through transmission test. In either arrangement, the test apparatus moves the one or more transducers into engagement with the particulate filter to test from a first discrete location along a surface of the particulate filter. After the test is performed, the test apparatus may reposition the one or more transducers to test from a second discrete location along the surface of the particulate filter. While this inspection method may prove successful at detecting internal flaws at the tested locations, it ultimately tests only a small volume of the particulate filter. Testing more locations across the filter surface is possible, but requires repositioning of the one or more ultrasonic transducers, which undesirably increases inspection time.

The present disclosure is directed to one or more of the problems set forth above.

SUMMARY OF THE DISCLOSURE

In one aspect, a method of detecting an internal flaw in a particulate filter includes a step of coupling an ultrasonic transducer with the particulate filter. The method also includes a step of moving at least one of the ultrasonic transducer and the particulate filter relative to the other. Coupling of the ultrasonic transducer with the particulate filter is maintained during the moving step. Ultrasonic energy is transmitted from the ultrasonic transducer through a majority of a volume of the particulate filter. The method also includes a step of determining if the particulate filter includes an internal flaw using the ultrasonic energy.

In another aspect, a system for detecting an internal flaw in a particulate filter includes a coupling medium for coupling the particulate filter with an ultrasonic transducer. A support fixture moves at least one of the particulate filter and the ultrasonic transducer relative to the other while maintaining coupling. The ultrasonic transducer is configured to transmit ultrasonic energy through a majority of a volume of the particulate filter. A flaw detection device determines if the particulate filter includes an internal flaw using the ultrasonic energy.

DETAILED DESCRIPTION

Figure 1:
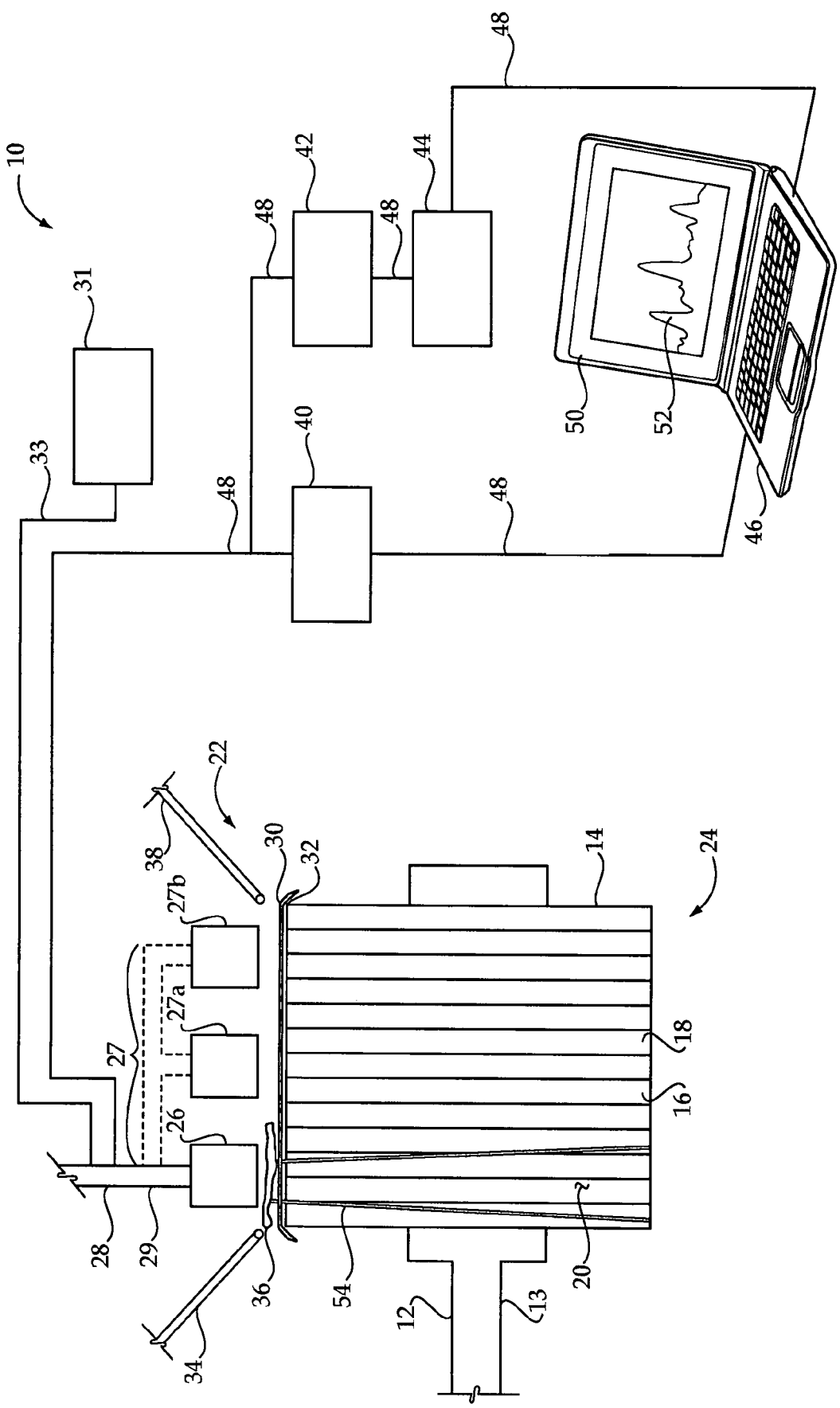
FIG. 1 is a side diagrammatic view of a system for detecting an internal flaw in a particulate filter according to the present disclosure.

An exemplary embodiment of a system 10 for detecting an internal flaw in a particulate filter is shown generally in FIG. 1. The system 10 may include a support fixture 12 for supporting a particulate filter 14. The particulate filter 14, such as, for example, a diesel particulate filter, is shown in cross section and typically includes a catalyst substrate or filter. The filter may include a honeycomb structure with thin walls defining longitudinal passages that extend from a gas inlet to a gas outlet of the filter. Although only a limited number of passages are shown, such as passages 16 and 18, it should be appreciated that a typical filter may comprise numerous passages. Adjacent passages are blocked at opposite ends, respectively, and open at the other to force exhaust gases entering the filter through an open passage to pass through the thin walls and exit the filter through a different open passage. Particulate matter within the exhaust gases is then trapped within the passage walls. As should be appreciated, internal flaws, such as, for example, crack 20, may form within the thin, delicate structure of the filter during manufacturing, catalyst coating, packaging, handling, regeneration, or any other similar process. Although a specific particulate filter 14 is described, it should be appreciated that any device that filters particulate matter from exhaust gases and is subject to internal flaws, such as cracks, is contemplated for use with the system 10 of FIG. 1.

The support fixture 12 may include any device or structure for supporting the particulate filter 14. The support fixture 12 may include an arm 13 extending from a base (not shown) that has an annular ring or other structure on the end thereof for frictionally engaging opposite ends of the particulate filter 14. Alternatively, the support fixture 12 may include a surface, such as a turntable type structure, for supporting the particulate filter 14 on a top portion thereof. Any alternative structure for facilitating a relatively fixed or movable position of the particulate filter 14 is also contemplated.

Figure 2:
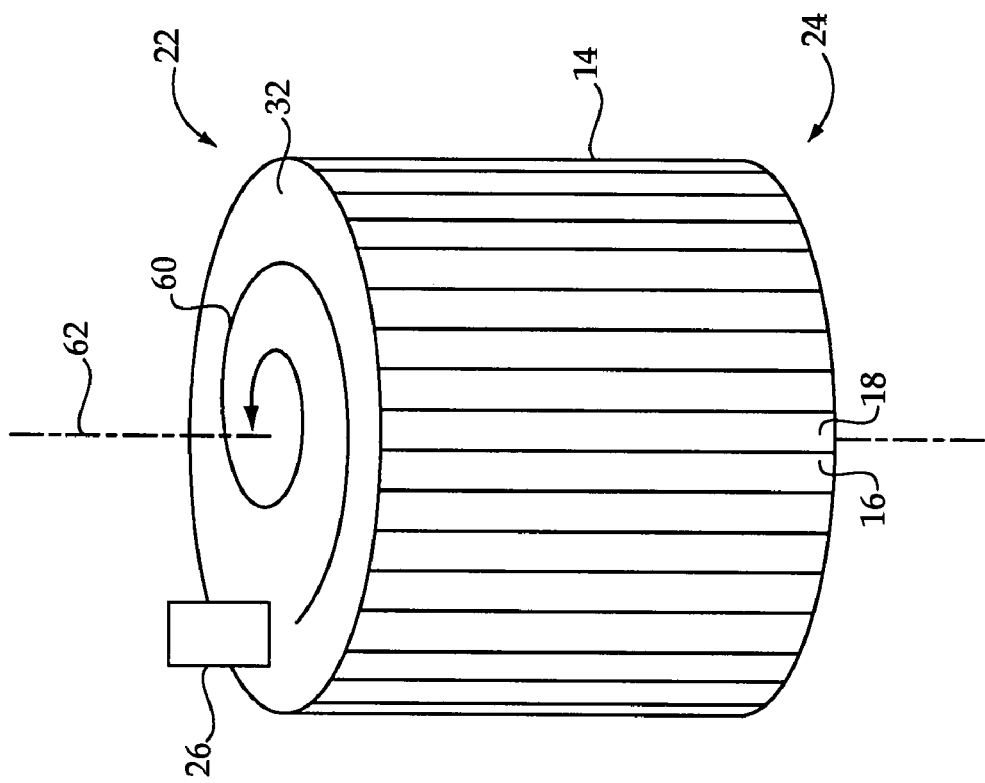
FIG. 2 is a side perspective view of an ultrasonic transducer movement pattern over the particulate filter of FIG. 1 according to the present disclosure.

It may be desirable to position or orient the particulate filter 14 vertically with a first end 22 facing upward and a second end 24 facing downward, as shown in FIG. 2. Alternatively, however, it may be desirable to position the particulate filter 14 with the second end 24 facing upward and the first end 22 facing downward. Further, it may be desirable to position the particulate filter 14 horizontally or at any other desired orientation. It should be appreciated that the first end 22 may represent a gas inlet of the particulate filter 14, while the second end 24 may represent a gas outlet of the particulate filter 14. Alternatively, the second end 24 may comprise the gas inlet and the first end 22 may comprise the gas outlet.

The system 10 also includes an ultrasonic transducer 26. Ultrasonic transducers are well known and may include any device for producing ultrasonic energy. The ultrasonic transducer 26 may, for example, include a single transducer, an array of transducers, or may even be a phased-array ultrasonic transducer. It should be appreciated that the ultrasonic transducer 26 may include a one-dimensional or a two-dimensional array of transducers and/or elements extending across a face of the particulate filter 14, or any other alternative arrangement of transducers or elements. An array 27 of transducers, including ultrasonic transducer 26 and additional transducers 27a and 27b, is shown in phantom in FIG. 1.

A phased-array transducer is also contemplated for the ultrasonic transducer 26 of system 10. A phased-array transducer is also well known and includes a plurality of elements, such as piezoelectric elements, for producing sound and/or ultrasound in response to an applied voltage. For a transducer array or phased-array transducer implementation, including the array 27 shown in phantom, it may be desirable to manipulate the amplitude and phase of the driving voltages applied to each transducer or element to direct the sound or ultrasound to targeted areas of the particulate filter 14. It may also be desirable to produce sound or ultrasound energy having various waveform shapes, such as, for example, pulse or tone burst.

The system 10 may also include a support fixture 28 for supporting the ultrasonic transducer 26. The support fixture 28 may include any device or structure for supporting the ultrasonic transducer 26. The support fixture 28 may also include an arm 29 extending from a base (not shown) that is fixedly attached to the ultrasonic transducer 26. The base may include a machine or other device for controlling operation of the ultrasonic transducer 26 and may be integral with the ultrasonic transducer 26. Any alternative structure for facilitating a relatively fixed or movable position of the ultrasonic transducer 26 is also contemplated.

At least one of the ultrasonic transducer support fixture 28 and the particulate filter support fixture 12 may be movable with respect to the other, such as via a plurality of conventional computer controlled actuators controlled by electronic controller 31. The electronic controller 31 may communicate with actuators (not shown) or directly with the ultrasonic transducer support fixture 28 wirelessly or via communication line 33. The particulate filter 14 may first be supported by support fixture 12 and, thereafter, moved into engagement with the ultrasonic transducer 26. Alternatively, however, the ultrasonic transducer 26 may be moved into engagement with the particulate filter 14. Ultimately, the ultrasonic transducer 26 is coupled with the particulate filter 14 via one or more coupling media.

Coupling media are used to transmit the ultrasonic energy from the ultrasonic transducer 26 to the particulate filter 14. A coupling medium, such as a self-adhesive film 30, may be provided on a surface 32 of the particulate filter 14 for transferring ultrasonic energy from the ultrasonic transducer 26. In addition, the self-adhesive film 30 may serve to protect the delicate structure of the particulate filter 14 during testing using the ultrasonic transducer 26 and may provide a means for preventing contamination of the particulate filter 14. The self-adhesive film 30 may adhere to all or a portion of a surface 32 of the particulate filter 14 and may adhere beyond the edges of the surface 32. The film 30 may comprise any number of deformable and/or durable materials, such as, for example, plastic, paper, or rubber. In the illustrated embodiment, the self-adhesive film 30 prevents contamination of the filter while facilitating ultrasonic transmission. It may be desirable for the selected material to provide a smooth, planar surface. Although a self-adhesive film 30 is shown, it should be appreciated that a coupling medium of any material may be used to prevent a high attenuation of the ultrasonic energy, such as that caused by air.

An additional coupling medium may be provided between the ultrasonic transducer 26 and the self-adhesive film 30. For example, a liquid introduction device 34 may be provided for continuously circulating a liquid 36, such as water, between the ultrasonic transducer 26 and the self-adhesive film 30. To prevent a large amount of liquid 36 from collecting, a liquid collection device 38 may also be provided to collect the liquid 36 that has circulated across a surface of the self-adhesive film 30. It should be appreciated that the liquid introduction device 34 may include a hose, supply line, brush, or any other know means of providing or transporting liquid 36 to a designated area. It should also be appreciated that the liquid collection device 38 may include any known means for gathering the liquid 36 that has been provided. It may be desirable to limit the amount of liquid to a surface of the self-adhesive film 30 and prevent the liquid from reaching the porous structure of the particulate filter 14. Although liquid 36 is shown in the illustrated embodiment, it should be appreciated that a gel or other similar substance is also contemplated. To achieve consistent acoustic coupling during relative movement of the ultrasonic transducer 26 and the particulate filter 14, the ultrasonic transducer 26 may or may not be in direct contact with the self-adhesive film 30.

Once the ultrasonic transducer 26 is sufficiently coupled to the particulate filter 14, a pulse echo sound or ultrasound measurement may be taken. Electrical energy from a pulser unit 40 excites the ultrasonic transducer 26, thereby generating ultrasonic energy into the particulate filter 14 through a consistent coupling medium 30. Specifically, the ultrasonic energy may be emitted from the ultrasonic transducer 26 into the particulate filter 14, and the returning energy or waves that are received by the ultrasonic transducer 26, processed by a receiver unit 42, and digitized by an analog-to-digital (A/D) computer card 44 may be analyzed. If an internal flaw, such as, for example, crack 20, is present, the ultrasound waves will bounce off of the edges defining the flaw and be seen in the returned energy or signal. It should be appreciated that, although a pulse echo measurement is described, a through transmission or any other type of sound or ultrasound measurement is also contemplated. With a through transmission measurement, the acoustic energy is sent the entire way through the particulate filter 14 and received by an additional ultrasonic transducer positioned on an opposite side, such as second end 24, of the particulate filter 14. Internal flaws, such as crack 20, will cause attenuation due to the crack gap in the ultrasonic energy that can be observed in the received energy or signal.

The ultrasonic energy that is collected by the ultrasonic transducer 26 and received by the receiver unit 42 may be digitized by the A/D computer card 44, as should be appreciated by those skilled in the art, and transmitted to a computer workstation 46 wirelessly or via a communication line 48. Specifically, the receiver unit 42 may transform the reflected ultrasonic energy into electrical signals and then pass the electrical signals through the A/D computer card 44, where they are digitized. The digitized signals may then be transmitted to the computer workstation 46 having a display 50. It should be appreciated that the pulser unit 40, receiver unit 42, and A/D computer card 44 may all communicate via one or more communication lines, such as the communication line 48. It should also be appreciated that the functions provided by the pulser unit 40, receiver unit 42, and A/D computer card 44 may be performed by a single machine or device, such as, for example, the computer workstation 46.

Software may be provided on the computer workstation 46 that plots the digitized signals on a graph 52 that may be viewed on the display 50. Data displayed on the graph 52 may be provided in real-time or may be stored for later display. Software analysis and/or manual analysis may be used to determine the existence of an internal flaw using the graph 52, representative of the reflected ultrasonic energy. It should be appreciated that software may also be utilized to help process or filter acoustic signal data to reduce sensitivity to noise and other interferences within the reflected energy. In addition, the computer workstation 46 may be used to direct the movement of the ultrasonic transducer 26 and/or the particulate filter 14 via the ultrasonic transducer support fixture 28 and/or the particulate filter support fixture 12.

Sound or ultrasound measurements may further be used to determine the actual or approximate location and size of a detected internal flaw or crack. For example, the location of an internal flaw or crack can be obtained by accurately measuring the time required for acoustic energy to travel through the particulate filter 14 and reflect from either a surface at the opposite end of the particulate filter, such as second end 24, or an internal flaw, such as the crack 20. Specifically, the amount of distance between peaks on the graph 52 shown on display 50 may be used to locate any internal flaws.

It may be desirable to perform pulse echo or through transmission measurements at multiple locations across the surface 32 of the particulate filter 14 to test a majority, if not all, of a volume of the particulate filter 14. To test from multiple locations, it may be desirable to move at least one of the ultrasonic transducer 26 and the particulate filter 14 relative to the other. By utilizing the coupling media described above, or other similar coupling media, the ultrasonic transducer 26 and the particulate filter 14 may remain coupled while one of the ultrasonic transducer 26 and the particulate filter 14 is moved relative to the other.

Ultrasonic energy may be continuously transmitted from the ultrasonic transducer 26 through the particulate filter 14 during the movement. Alternatively, however, the ultrasonic energy may be intermittently transmitted while one of the ultrasonic transducer 26 and the particulate filter 14 moves relative to the other. As should be appreciated, the ultrasonic transducer 26 may transmit ultrasonic energy along a plurality of pathways through the particulate filter 14, wherein each pathway, such as pathway 54, includes a cylindrical pathway having a diameter approximately equal to a width of the ultrasonic transducer 26 and extending from the first end 22 of the particulate filter 14 to the second end 24 of the particulate filter 14. Additionally, the ultrasonic transducer 26 and/or the particulate filter 14 may be movable, such as via movement controlled by the electronic controller 31, in such a way that the ultrasonic transducer 26 remains coupled to the particulate filter 14 in a plurality of locations comprising a predetermined pattern 60, shown in FIG. 2, such as a spiral pattern, a rectangular pattern, a cylindrical pattern, or any other desired pattern. Although a specific pattern of movement is described, it should be appreciated that any pattern of movement facilitating the transmission of acoustic energy through a majority of a volume of the particulate filter 14 is contemplated.

INDUSTRIAL APPLICABILITY

Referring to FIGS. 1 and 2, a particulate filter 14 typically includes a catalyst substrate or filter. The filter includes thin walls defining longitudinal passages that extend from a gas inlet to a gas outlet. Although only a limited number of passages are shown, such as passages 16 and 18, it should be appreciated that a typical filter comprises numerous passages. The passages are blocked at one end and open at the other to force exhaust gases entering the filter through an open passage to pass through the thin walls and exit the filter through a different open passage. Particulate matter within the exhaust gases is then trapped within the passage walls. It is well known that, during the filter substrate production, catalyst coating, packaging, and regeneration processes, occasional internal defects, such as cracks and internal voids, can occur in the filter structures. When a crack occurs in cell walls of the substrate, the crack can significantly affect the durability of the filter and can result in a substantial deterioration in the ability of the filter to trap particles according to expectations and specifications.

Figure 3:
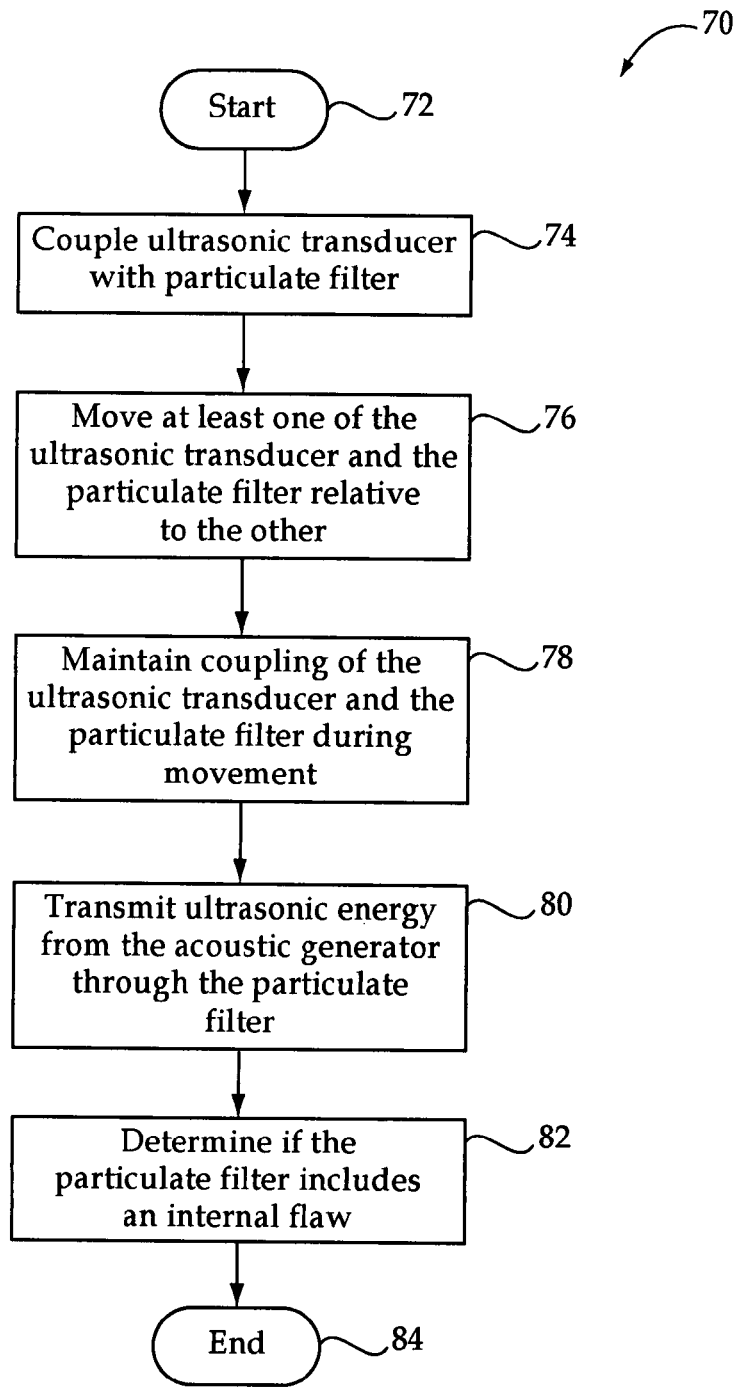
FIG. 3 is a flow chart of one embodiment of a method for detecting an internal flaw in a particulate filter according to the present disclosure.

Utilizing the system and method for detecting internal flaws in a particulate filter, such as particulate filter 14, according to the present disclosure provides a means for discovering internal cracks and voids within the filter in a timely and non-destructive manner. The method may be executed manually or via execution of software in an electronic controller 31. Turning to FIG. 3, there is shown a flow chart 70 representing an exemplary method of detecting internal flaws in a particulate filter 14 utilizing the system 10 of FIG. 1. The method begins at a START, Box 72. From Box 72, the method proceeds to Box 74, which includes the step of coupling an ultrasonic transducer 26 with the particulate filter 14. The ultrasonic transducer 26 may, for example, include a single transducer (as shown), a transducer array (as shown in phantom at 27), or a phased-array transducer, and may be coupled to the particulate filter 14 using a self-adhesive film 30 that is adhered to a surface 32 of the particulate filter 14.

A liquid 36, such as water, may also be provided as a coupling medium and may be continuously circulated between the ultrasonic transducer 26 and the self-adhesive film 30. Alternatively, a small amount of liquid 36 may be brushed onto a surface of the self-adhesive film 30. The self-adhesive film 30 couples ultrasonic energy from the liquid 36 to the filter and prevents the liquid 36 from entering the particulate filter 14. Although specific examples are given, it should be appreciated that any coupling media, including any liquid and/or membrane that maximize the use of the ultrasonic energy, maintain consistent coupling during relative motion of the particulate filter 14 and the ultrasonic transducer 26, and enable or facilitate cost effective manual or automatic implementation of the method, are contemplated.

To facilitate coupling, one of the ultrasonic transducer 26 and the particulate filter 14 may be moved into engagement with the other. Specifically, at least one of the support fixtures 12 and 28 may be movable to position the ultrasonic transducer 26 and the particulate filter 14 to allow sufficient coupling via the self-adhesive film 30 and liquid 36.

After the ultrasonic transducer 26 is coupled with the particulate filter 14, the method proceeds to Box 76. At Box 76, at least one of the ultrasonic transducer 26 and the particulate filter 14 is moved relative to the other. Specifically, at least one of the particulate filter support fixture 12 and the ultrasonic transducer support fixture 28 may move the particulate filter 14 or the ultrasonic transducer 26, respectively, relative to the other. For example, the particulate filter support fixture 12 may spin, such as via a turntable, the particulate filter 14 about a spin axis 62, as shown in FIG. 2. The ultrasonic transducer support fixture 28 may then move the ultrasonic transducer 26 along a line that is perpendicular to the spin axis 62. This movement may result in the ultrasonic transducer 26 contacting, directly or indirectly, the particulate filter 14 at a plurality of locations corresponding to a predetermined pattern 60, such as a spiral pattern, as shown. Alternative movements and patterns are also contemplated.

At Box 78, coupling of the ultrasonic transducer 26 to the particulate filter 14 is maintained while one of the ultrasonic transducer 26 and the particulate filter 14 is moved relative to the other. Specifically, the coupling media that are selected should allow continuous or intermittent movement of the one of the ultrasonic transducer 26 and the particulate filter 14 while preventing significant variations and/or attenuation of the ultrasonic energy transmitted from the ultrasonic transducer 26 through the particulate filter 14. For example, the self-adhesive film 30 provides a smooth, planar filter surface free of air gaps that, when used with the liquid 36, facilitates propagation of the acoustic energy from the ultrasonic transducer 26 through the particulate filter 14. In addition, the coupling media provide low friction to allow ease of rapid movement of one of the ultrasonic transducer 26 and the particulate filter 14 relative to the other. The self-adhesive film 30 also protects the particulate filter 14 from liquid contamination.

From Box 78, the method proceeds to Box 80, which includes the step of transmitting energy provided by a pulser unit 40 to the ultrasonic transducer 26 and through the particulate filter 14. Ultrasonic energy may be continuously or intermittently transmitted and received via the ultrasonic transducer 26 while one of the ultrasonic transducer 26 and the particulate filter 14 is moved relative to the other. Specifically, ultrasonic energy may be transmitted along a plurality of pathways, such as pathway 54, while one of the ultrasonic transducer 26 and the particulate filter 14 is moved relative to the other. Additionally, the ultrasonic transducer 26 and/or the particulate filter 14 may be movable in such a way that the ultrasonic transducer 26 remains coupled to the particulate filter 14 in a plurality of locations comprising a predetermined pattern 60, shown in FIG. 2, such as a spiral pattern, a rectangular pattern, a cylindrical pattern, or any other desired pattern. Although a specific pattern of movement is described, it should be appreciated that any pattern of movement facilitating the transmission of ultrasonic energy through a majority of a volume of the particulate filter 14 is contemplated. It should also be appreciated that the pattern 60 and cumulative scans may comprise more than ninety percent of the volume of the particulate filter 14.

The ultrasonic energy that is received by a receiver unit 42 from the ultrasonic transducer 26 may be transmitted to a computer workstation 42 via a communication line 48. Specifically, the receiver unit 42 may transform the reflected ultrasonic energy into electrical signals and then pass the electrical signals through an analog-to-digital (A/D) computer card 44, where they are digitized. The digitized signals may then be transmitted to the computer workstation 46. A display 50 of the computer workstation 46 may provide a graph 52 that plots the digitized signals. From Box 80, the method proceeds to Box 82. At Box 82, the method determines if the particulate filter 14 includes an internal flaw using the ultrasonic energy or, more specifically, the graph 48. Software analysis and/or manual analysis may be used to determine the existence of an internal flaw using the reflected ultrasonic energy depicted by graph 48. It should be appreciated that software filters may also be utilized to help reduce sensitivity to interference within the reflected energy. Although the signal data may preferably used in real-time, it should be appreciated that the data may be stored for later processing and association with a particular filter, such as particulate filter 14. After the ultrasonic energy has been used to detect internal flaws in the particulate filter, the method proceeds to an END, at Box 84.

It should be appreciated that the system and method of the present disclosure provide a timely means for detecting internal flaws in a particulate filter 14 using acoustic energy. Specifically, coupling is maintained while one of the ultrasonic transducer 26 and the particulate filter 14 is moved relative to the other. During the movement, ultrasonic energy is continuously transmitted through the particulate filter 14 and evaluated by the computer workstation 42. Both the movement, facilitated through sufficient and consistent coupling, and the continuous transmission of ultrasonic energy allow for at least about ninety percent of a volume of the particulate filter 14 to be loaded into system 10, tested for internal flaws, and removed in less than about two minutes.

Obvious advantages to the present disclosure include the automation of the internal flaw detection process of particulate filters, which allows for a quicker inspection time for the filters. The automation is possible through use of the coupling arrangement described herein, including the utilization of a self-adhesive film 30 and a liquid 36. The self-adhesive film 30 prevents liquid contamination of the filter 14, while the vertical orientation of the filter 14 in the system 10 allows for a simplified liquid circulation process. It should be appreciated that numerous other advantages, besides the ones stated herein, are also achieved from the present disclosure.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A method of detecting an internal flaw in a particulate filter, comprising:
    coupling an ultrasonic transducer with the particulate filter;
    moving at least one of the ultrasonic transducer and the particulate filter relative to the other;
    maintaining coupling of the ultrasonic transducer with the particulate filter during the moving step;
    transmitting ultrasonic energy from the ultrasonic transducer through at least about 90 percent of the volume of the particulate filter in less than about two minutes; and
    determining if the particulate filter includes an internal flaw using the ultrasonic energy.

2. The method of claim 1, wherein the coupling step includes adhering a self-adhesive film over a face of the particulate filter.

3. The method of claim 2, wherein the coupling step further includes providing a liquid between the ultrasonic transducer and the self-adhesive film.

4. The method of claim 3, wherein the providing step includes continuously circulating the liquid to an area between the ultrasonic transducer and the self-adhesive film.

5. The method of claim 1, wherein the transmitting step is performed continuously during the moving step.

6. The method of claim 1, wherein the moving step includes moving the at least one of the ultrasonic transducer and the particulate filter relative to the other so that the ultrasonic transducer maintains coupling with the particulate filter at a plurality of locations corresponding to a predetermined pattern.

7. The method of claim 6, further including vertically orienting the particulate filter.

8. The method of claim 7, wherein the moving step further includes spinning the particulate filter about a spin axis.

9. The method of claim 8, wherein the moving step further includes moving the ultrasonic transducer along a line, wherein the line is perpendicular to the spin axis of the particulate filter.

10. A system for detecting an internal flaw in a particulate filter, comprising:
    a coupling medium for coupling the particulate filter with an ultrasonic transducer;
    a support fixture for moving at least one of the particulate filter and the ultrasonic transducer relative to the other while maintaining coupling;
    wherein the ultrasonic transducer is configured to transmit ultrasonic energy through at least about 90 percent of the volume of the particulate filter in less than about two minutes; and
    a flaw detection device for determining if the particulate filter includes an internal flaw using the ultrasonic energy.

11. The system of claim 10, wherein the coupling medium includes a self-adhesive film adhered over the face of the particulate filter.

12. The system of claim 11, wherein the coupling medium further includes a liquid provided between the ultrasonic transducer and the self-adhesive film.

13. The system of claim 12, further including at least one of a liquid introduction device and a liquid collection device for continuously circulating the liquid to an area between the ultrasonic transducer and the self-adhesive film.

14. The system of claim 10, wherein the ultrasonic transducer is one of an array of ultrasonic transducers and a phased-array transducer.

15. The system of claim 10, wherein the ultrasonic transducer is configured to transmit ultrasonic energy through the particulate filter while the at least one of the particulate filter and the ultrasonic transducer moves relative to the other.

16. The system of claim 10, wherein the support fixture is configured to move the at least one of the ultrasonic transducer and the particulate filter relative to the other so that the ultrasonic transducer maintains coupling with the particulate filter at a plurality of locations corresponding to a predetermined pattern.

* * * * *